United States Patent [19]

Wright et al.

[11] 4,093,627

[45] June 6, 1978

[54] 3-[(4-CHROMANYLIDENE)AMINO]-2-OXAZOLIDINONES

[75] Inventors: George C. Wright; Marvin M. Goldenberg, both of Norwich, N.Y.

[73] Assignee: Morton-Norwich Products, Inc., Norwich, N.Y.

[21] Appl. No.: 812,126

[22] Filed: Jul. 1, 1977

[51] Int. Cl.² ............................................ C07D 263/26
[52] U.S. Cl. .................................................. 260/307 C
[58] Field of Search .................................... 260/307 C

[56] References Cited

U.S. PATENT DOCUMENTS

| | | | |
|---|---|---|---|
| 2,847,416 | 8/1958 | Gever | 260/307 |
| 3,288,787 | 11/1966 | Massaroli | 260/240 |
| 3,318,878 | 5/1967 | Dunn | 260/240 |

OTHER PUBLICATIONS

Smith, P. A. S., "Open–Chain Nitrogen Compounds," vol. 1 (1965), W. A. Benjamin, Inc., pp. 26–27.

*Primary Examiner*—Raymond V. Rush
*Attorney, Agent, or Firm*—Anthony J. Franze

[57] ABSTRACT

A series of 3-[(4-chromanylidene)amino]-2-oxazolidinones are useful as gastric antisecretory agents.

4 Claims, No Drawings

3-[(4-CHROMANYLIDENE)AMINO]-2-OXAZOLIDINONES

This invention is concerned with chemical compounds. More particularly, it relates to a series of 3-[(4-chromanylidene)amino]-2-oxazolidinones of the formula:

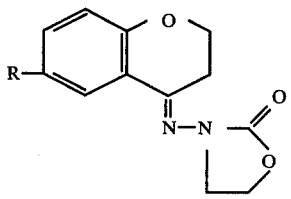

wherein R is hydrogen, methoxy or nitro.

These compounds are useful as gastric antisecretory agents. Thus, when administered per os at a dose of about 100 mg/kg suspended in a suitable physiologically acceptable vehicle such as 5% aqueous carboxymethylcellulose about one hour prior to pylorus ligation of the rat stomach, gastric acid output is inhibited to the extent of from 56–77% and the volume of gastric secretion inhibited to the extent of from 38–52%.

These compounds can be readily formulated in a variety of pharmaceutical dosage forms such as tablets, suspensions, elixirs, capsules and the like using commonly employed pharmaceutical excipients and adjuvants with which there is no incompatibility.

In order that this invention may be readily available to and understood by those skilled in the art, the following examples illustrate the now preferred method for the preparation of the compounds thereof.

EXAMPLE I

3-[(4-Chromanylidene)amino]-2-oxazolidinone

A 62-g (0.61 mole) portion of 3-amino-2-oxazolidinone was charged in a 500-ml, 3-necked flask equipped with a thermometer, stirrer and reflux condenser, and treated successively with 92 ml of $H_2O$, 8 ml of 10% HCl and 42 g (0.28 mole) of 4-chromanone in 200 ml ethanol. The reaction mixture was refluxed for 36 hr, stripped in vacuo to one-half volume and cooled in the refrigerator overnight. The slurry was filtered and the white crystalline solid washed with 50 ml of isopropanol then 200 ml of ether and dried. M.p. 105°–108°. Yield: 44 g (68%).

The filtrate was extracted with 250 ml of $CHCl_3$, and the $CHCl_3$ extract dried over $MgSO_4$, filtered, and stripped in vacuo. The residue was slurried in 100 ml of ether, allowed to stand 3 hr, filtered, and the product dried. M.p. 50°–62°. Yield: 9 g (14%). Then the combined crude products were recrystallized from 350 ml of isopropanol, washed with 40 ml of isopropanol, 150 ml ether and dried. M.p. 111°–113°. Yield: 40 g (62%).

Anal. Calcd. for $C_{12}H_{12}N_2O_3$: C, 62.06; H, 5.21; N, 12.06. Found: C, 62.02; H, 5.24; N, 12.08.

EXAMPLE II

3-[(6-Methoxy-4-chromanylidene)amino]-2-oxazolidinone

A solution of 62 g (0.61 mole) of 3-amino-2-oxazolidone in 650 ml of benzene was treated with 15 drops of HCl (isopropanol) solution using mechanical stirring, and refluxed until all water was removed via a Dean-Stark trap. The solution was then treated with 107 g (0.60 mole) of 6-methoxy-4-chromanone and refluxed for 11.5 hr. A 9.6 ml portion of water (theory: 10.8 ml) was collected. The reaction mixture was stripped of benzene under the water pump. The residue was taken up in 200 ml of 1:1 isopropanol:ether, stored 24 hr at room temperature, refrigerated overnight and filtered. The resultant cream-colored solid was washed with 125 ml of isopropanol, ether, and dried. M.p. 54°–64°; yield: 115 g (73%).

The crude product was recrystallized from 340 ml of isopropanol (Darco), washed with 75 ml of isopropanol, ether and dried. M.p. 67°–71°; Yield: 88 g (56%).

Anal. Calcd. for $C_{13}H_{14}N_2O_4$: C, 59.53; H, 5.38; N, 10.68. Found: C, 59.57; H, 5.28; N, 10.56.

EXAMPLE III

3-[(6-Nitro-4-chromanylidene)amino]-2-oxazolidinone

An 85 g (0.44 mole) portion of 6-nitro-4-chromanone in 460 ml of benzene was treated with 1 ml of HCl (isopropanol) solution, using mechanical stirring, and refluxed until all water was removed via a Dean-Stark trap. The solution was then treated with 46 g (0.46 mole) of 3-amino-2-oxazolidinone and refluxed for 2.6 hr. A 7.9 ml portion of water was collected (theory: 7.9 ml). The reaction mixture was filtered hot, cooled to 10°–11° for 3 hrs. and filtered. The orange crystalline solid was washed with 100 ml of benzene, ether and dried, m.p. 168°–170°. Yield: 107 g (88%).

The product was recrystallized from 650 ml of nitromethane (Darco), washed with 100 ml of cold nitromethane, ether and dried, m.p. 170°–171°, Yield: 84 g (69%).

Anal. Calcd. for $C_{12}H_{11}N_3O_5$: C, 51.99; H, 4.00; N, 15.16. Found: C, 51.96; H, 4.03; N, 15.14.

What is claimed is:

1. A compound of the formula:

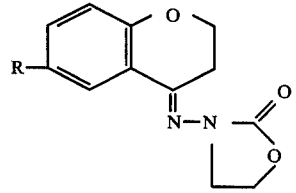

wherein R is hydrogen, methoxy or nitro.

2. The compound 3-[(4-chromanylidene)amino]-2-oxazolidinone.

3. The compound 3-[(6-methoxy-4-chromanylidene)amino]-2-oxazolidinone.

4. The compound 3-[(6-nitro-4-chromanylidene)amino]-2-oxazolidinone.

* * * * *